United States Patent
Gouliaev et al.

(10) Patent No.: US 6,500,954 B1
(45) Date of Patent: Dec. 31, 2002

(54) SYNTHESIS OF 5- OR 8-BROMOISOQUINOLINE DERIVATIVES

(75) Inventors: Alex Haahr Gouliaev, Veksø Sj. (DK); William Hansen, København NV (DK)

(73) Assignee: NeuroSearch A/S, Ballerup (DK)

( * ) Notice: Subject to any disclaimer, the term of this patent is extended or adjusted under 35 U.S.C. 154(b) by 0 days.

(21) Appl. No.: 09/685,025

(22) Filed: Oct. 10, 2000

Related U.S. Application Data

(63) Continuation of application No. PCT/DK99/00347, filed on Jun. 22, 1999.

(30) Foreign Application Priority Data

Jun. 22, 1998 (DK) ......................................... 1998 00884

(51) Int. Cl.[7] ............................................. C07D 217/00
(52) U.S. Cl. ...................................................... 546/139
(58) Field of Search ......................................... 546/139

(56) References Cited

PUBLICATIONS

Gordon et. al., "The Swamping Catalyst Effect. VI. The Halogenation of Isoquinoline and Quinoline", J. Org. Chem. 29 (2), pp. 329–332.*

Gordon et al., Holgenation of Isoquinoline, vol. 29, pp. 329–332 (1964).
Mathison et al., Journal of Organic Chemistry, vol. 39, No. 22, pp. 3210–5 (1974).
Rey et al., Helvetica Chemica Acta, vol. 68, pp. 1828–1834 (1985).
De La Mare et al., J. Chem. Soc., pp. 561–565 (1960).
Dickerman et al., Chemistry and Industry, pp. 360–361 (1958).
Butler et al., Trans. KY Acad., vol. 38, No. 15, pp. 15–20 (1977).
Glyde et al., J. Chem. Soc., pp. 1783–1791 (1975).
Robinson, J. Am. Chem. Soc., vol. 69, pp. 1942–1943 (1947).
Osborn et al., Studies of the Amino–isoquinolines . . . , pp. 4191–4204 (1956).

* cited by examiner

*Primary Examiner*—Alan L. Rotman
*Assistant Examiner*—Binta Robinson
(74) *Attorney, Agent, or Firm*—Birch, Stewart, Kolasch & Birch, LLP

(57) ABSTRACT

The present invention is directed to a method of preparing bromoisoquinoline derivatives, in particular 5- or 8-bromoisoquinoline derivatives. Bromoisoquinoline derivatives, and in particular 5-bromoisoquinoline and 5-bromo-8-nitroisoquinoline derivatives, are key intermediates in the synthesis of pharmaceutical compounds.

18 Claims, No Drawings

SYNTHESIS OF 5- OR 8-BROMOISOQUINOLINE DERIVATIVES

This Application is a Continuation of PCT/OK99/00347 filed Jun. 22, 1999

TECHNICAL FIELD

The present invention is directed to a method of preparing bromoisoquinoline derivatives, in particular 5- or 8-bromoisoquinoline derivatives. Bromoisoquinoline derivatives, and in particular 5-bromoisoquinoline and 5-bromo-8-nitroisoquinoline derivatives, are key intermediates in the synthesis of pharmaceutical compounds.

BACKGROUND ART

Bromoisoquinoline derivatives, and in particular 5-bromoisoquinoline and 5-bromo-8-nitroisoquinoline derivatives, are key intermediates in the synthesis of pharmaceutical compounds.

Direct bromination of the rather electron poor isoquinoline system using elemental bromine can only be achieved by the co-use of catalysts. One such method has been described by Gordon and Pearson [see Gordon M. & Pearson D. E., *J. Org. Chem.* 1964 29 329; and Butler J. L., Bayer F. L. & Gordon M., *Trans K.Y. Acad. Sci.*, 1977 38 15] by which 5-bromoisoquinoline was synthesised by the addition of liquid bromine to a melt of isoquinoline and aluminium chloride at 75° C., giving 43–46% yield of product after re-crystallisation. The method has been modified by Mathison and Morgan [Mathison I. W. & Morgan P. H., *J. Org. Chem.*, 1974 39 3210], who used gaseous bromine and obtained a yield of 42%. A similar method using liquid bromine and AlBr$_3$ has been described by Rey et al. [see Rey M., Vergnani T. & Dreiding A. S., *Helv. Chim. Acta.*, 1985 68 1828], giving a yield of 39%. Bromination using Br$_2$ and Ag$_2$SO$_4$ in H$_2$SO$_4$ could also be accomplished, however, only giving a yield of 23% [see Rey M., Vergnani T. & Dreiding A. S., *Helv. Chim. Acta.*, 1985 68 1828; De La Mare P. B. D. Kiamud-din M. & Ridd J. H., *J. Chem. Soc.*, 1960 561; and De La Mare P. B. D. Kiamud-din M. & Ridd J. H., *Chem. Ind. (London)*, 1958 361].

An indirect method for the synthesis of 5-bromoisoquinoline, makes uses of the fact, that nitration is much more easily achieved, i.e. nitration, reduction and finally diazotation gives 5-bromoisoquinoline [see Butler J. L., Bayer F. L. & Gordon M., *Trans K.Y. Acad. Sci.*, 1977 38 15; Glyde E. & Talor R., *J. Chem. Soc. Perkin Trans II*, 1975 1783; Robinson R. A., *J. Am. Chem. Soc.*, 1947 69 1942; and Osburn A. R., Schofield K. & Short L. N., *J. Chem. Soc.*, 1956 4191].

The direct bromination procedure tends to give mixtures of brominated products and in unsatisfactory yield, and none of the methods described are well suited for large scale work. The indirect method is not very suitable for large scale work especially due to the diazotation step.

SUMMARY OF THE INVENTION

In the present invention we describe a high yielding method for the synthesis of 5- or 8-bromoisoquinoline and its derivatives using cheap starting materials. The method of the invention is particularly well suited for large scale work operation and for accomplishing "one-pot" synthesis.

DETAILED DISCLOSURE OF THE INVENTION

The present invention provides a method of preparing bromoisoquinoline and its derivatives. More particularly, the invention provides a high yielding method for the synthesis of 5- or 8-bromoisoquinoline and its derivatives, in particular 5-bromo-8-nitroisoquinoline. Accordingly, in its most general aspect, the invention provides a process for the preparation of 5- or 8-bromoisoisoquinoline, or a derivative thereof, which process comprises the step of reacting isoquinoline, or a derivative thereof, with a brominating agent In the presence of a catalyst.

The Brominating Agent

The brominating agent used according to the present invention may be any suitable brominating agent. However, in a preferred embodiment, a suitable brominating agent is an agent of the general formula Z—Br, wherein Z represents a suitable leaving group.

In a most preferred embodiment the leaving group may be a secondary amino group of the general formula R$_2$N—Br, wherein R is alkyl, aryl, acyl or sulfonyl, or R$_2$N—Br describes a cyclic structure [e.g. N-bromosuccinimide (NBS), N,N'-dibromoisocyanuric acid (DBI) or N,N'-dibromohydantoin (DBH)]:

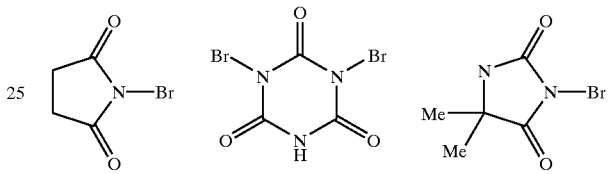

Catalyst and Catalytic Solvents

The catalyst contemplated in the method of the invention may be any suitable H$^+$ or a Lewis acid. The Lewis acid may in particular be a compound of the formula M'$_m$X$_{n'}$, where M' represents a metal, and X represents halogen. Preferred Lewis acids are e.g. BF$_3$, AlX$_3$, TiX$_4$, ZnX$_2$, MnX$_2$, FeX$_3$, FeX$_2$, SnX$_2$, PbX$_2$, SbX$_3$, and SbX$_5$.

The solvent is an acid with or without H$_2$O, e.g. FSO$_3$H, ClSO$_3$H, CF$_3$SO$_3$H, H$_2$SO$_4$, CH$_3$SO$_3$H, H$_3$PO$_4$, polyphosphoric acid, H$_3$PO$_3$, HXO$_4$, HXO$_3$, HXO$_2$, HXO, HX, CF$_3$COOH, CH$_3$COOH and others, where X represents halogen.

In a preferred aspect of the invention the solvent is an acid with or without H$_2$O i.e. HCl (0.1 N to conc.), CF$_3$SO$_3$H, H$_2$SO$_4$, CH$_3$SO$_3$H, CF$_3$COOH or CH$_3$COOH.

In another preferred aspect of the invention the solvent functions as a catalyst.

Nitrating Reagent

MNO3 is a nitrating reagent as known in the art, wherein M represents a metal or H$^+$. The active component being NO$_2^+$ formed in situ in the reaction mixture.

Process Conditions

The method of the invention may be conducted at temperatures ranging from −50° C. to 200° C. with the temperature range between −30° C. to −15° C. being the preferred for the preparation of the 5- or 8-bromoisoquinolines.

The method of the invention may be conducted from 0.1 g to 500 kg scale with the preferred scale being 1 g to 50 kg. Finally, the reaction may be conducted at 0.1 M to 5 M concentration with a preferred concentration of 0.5–1 M.

The method of the invention may be quenched after bromination giving 5-bromo or 8-bromoisoquinoline or continued by addition of metal nitrate, whereby 5-bromo-8-nitroisoquinoline or 8-bromo-5-nitroisoquinoline may be isolated from a "ONE POT" reaction.

The synthesis of 5-bromoisoquinoline and 5-bromo-8-nitroisoquinoline may in broad terms be described as a transformation of isoquinoline to 5-bromoisoquinoline using strong acid, preferably conc. $H_2SO_4$, and a brominating agent, preferably NBS. The bromination is preferably conducted at 0.5–1 M scale at a temperature of −30° C. to −15° C. 5-Bromoisoquinoline may be worked up and isolated as pure material or it may be further transformed, without prior isolation into 5-bromo-8-nitroisoquinoline by addition of potassium nitrate to the reaction mixture. Workup and recrystalization gives pure 5-bromo-8-nitroisoquinoline.

EXAMPLE

The invention is further illustrated with reference to the following examples which are not intended to be in any way limiting to the scope of the invention as claimed.

In the following we describe one selected set of optimised reaction conditions for both labscale and large scale production, making a compromise between yield (of the reaction), costs (of the solvent and the brominating agent) and availability (of the brominating agent).

5-Bromoisoquinoline.

Isoquinoline (15 ml; 128 mmol) was slowly added to a mechanically stirred solution of concentrated $H_2SO_4$ (130 ml) (Note 1) at −20° C., at such a speed that the temperature did not exceed +8° C. The reaction mixture was then re-cooled to −20° C., and solid N-bromosuccinimide (27.29 g; 153 mmol) (Note 2 and 3) was added at such a speed that the reaction temperature did not exceed −15°C. (Note 4). The reaction mixture was stirred at −20° C. until all isoquinoline was consumed (Note 5). The reaction was then allowed to warm to −9° C. over 20 min. The reaction mixture was poured onto 300 g of crushed ice and pH adjusted to 10 using 25% $NH_3$ (aq.), while the temperature was kept below 50–60° C. Extraction with diethyl ether (2×250 ml) filtration through celite and evaporation to dryness gave a red-brown oil which crystalized upon cooling. The precipitate was suspended in boiling heptane (300 ml) under rapid stirring and decanted while warm. This procedure was repeated with hexane (2×100 ml). The combined organic fractions was evaporated to dryness to give 18.2 g crude product as a slightly yellow powder. Recrystalization from heptane gave 15.2 g (59 % from 97% isoquinoline) of pure product as a slightly yellow powder. M.p. 82–83° C. (Litt. 82–83° C.[4], 79.5–80.5° C.[1], 82–84° C.[3,9], 83.0–83.5° C.[2], 83–85° C.[5]); $^1$H-NMR (DMSO-$d_6$): δ 9.38 (d, J=0.9 Hz); 8.67 (d, J=5.9 Hz); 8.21 (d, J=8.2 Hz); 8.16 (dd, $J_A$=0.9 Hz, $J_B$=7.5 Hz); 7.94 (d, J=5.9 Hz); 7.64 (t[†], J=7.8 Hz). [†] A dd with $J_A$=8.2 Hz and $J_B$=7.5 Hz was expected.

5-Bromo-8-nitroisoquinoline.

Isoquinoline (15 ml; 128 mmol) was slowly added to a mechanically stirred solution of concentrated $H_2SO_4$ (130 ml) (Note 1) at −20° C., at such a speed that the temperature did not exceed +8° C. The reaction mixture was then re-cooled to −20° C., and solid N-bromosuccinimide (27.29 g; 153 mmol) (Note 2 and 3) was added at such a speed that the reaction temperature did not exceed −15° C. (Note 4). The reaction mixture was stirred at −20 ° C. until all isoquinoline was consumed (Note 5). Solid $KNO_3$ (13 g; 128 mmol) was added in one portion, whereby the reaction temperature warmed up to −12° C. to −10° C. The reaction was stirred at −10° C. to −20° C. for 2 hours and then allowed to warm up to rt. The reaction mixture was poured onto 650 g of crushed ice and pH adjusted to 7.0 (Note 6) using 25% $NH_3$ (aq.), while the temperature was kept below +30° C. The mixture was left for precipitation for 1 h at rt. The yellow precipitate was isolated by filtration, washed on the filter with $H_2O$ (3×500 ml) and then dried by suction followed by air drying to give 27.1 g crude product. (Note 7).

Purification was achieved by either recrystalisation from heptane (A) or heptane/toluene (B).

A. The crude product was suspended in heptane (1500 ml), heated to reflux, and then filtered warm through celite. The filtrate was evaporated until precipitation occured (appoximate when 900 ml was left). It was then heated to reflux again and heptane (250 ml) was added to give a clear solution, which was slowly cooled and left for precipitation over night. Filtration and air drying to constant weight gave 22.8 g (73% from 97% pure isoquinoline) of pure 5-bromo-8-nitroisoquinoline as light yellow needles (Note 8).

B. The crude product was suspended in heptane/toluene (300 ml/150 ml) heated to reflux and then filtered warm through celite. The filtrate was evaporated until approximately 250 ml was left. The clear solution was slowly cooled and left for precipitation over night. Filtration and air drying to constant weight gave 21.7 g (69 % from 97% pure isoquinoline) of pure 5-bromo-8-nitroisoquinoline as light yellow needles (Note 8).

M.p. 137.5–139.5° C. (Litt. 138–139° C.[4], 138–140° C.[9], 139–141° C.[3]); $^1$H-NMR (DMSO-$d_6$): δ 9.81 (d, J=0.6 Hz); 8.87 (d, J=5.9 Hz); 8.39[†] (d, 8.1 Hz); 8.36[†] (d, 8.1 Hz); 8.16 (dd, $J_A$=0.6 Hz, $J_B$=5.9 Hz). [†] AB-system.

Notes

1. Different acids [HCl, $CF_3SO_3H$, $H_2SO_4$, $CH_3SO_3H$, $CF_3COOH$, $CH_3COOH$] were tested as solvents with or without the addition of $H_2O$. The reaction rate and 5- vs. 8-selectivity increases with acidity of the solvent. NBS decomposed in $CF_3SO_3H$. This was not the case with DBI. Isoquinoline decomposition increases with the amount of water present.

2. N-Bromosuccinimide was recrystalized (10 g in 100 ml $H_2O$) and air dried over night before use. Otherwise a substantial excess of NBS was needed to achieve fully conversion of isoquinoline with a concomitant increase in the amount of 5,8-dibromoisoquinoline.

3. The relative reactivity and selectivity of the brominating agents was DBI>NBS>DBH. NBS and DBH are commercially available and DBI is very easy to make from elemental bromine, lithium hydroxide and cyanuric acid according to the procedure of Gottardi.[10]

4. The reaction temperature is very important in order to achieve a high 5- vs. 8-selectivity and should not be above −15° C. during the bromination.

5. The reaction was monitored by TLC ($CH_2Cl_2$/EtOAc= 9/1). Isoquinoline was nearly or completely consumed after 4–5 h.

6. When pH was raised above 7.0 the reaction mixture started to darken.

7. The crude product was typically of the following composition:
5-Bromo-8-nitroisoquinolin/5,8-dibromoisoquinoline/ 5-nitroisoquinoline/8-bromo-5-nitroisoquinoline: 90–94%/2–5%/2–4%/0–1%.

8. The purified product was typically of the following composition:
5-Bromo-8-nitroisoquinolin/5,8-dibromoisoquinoline/ 5-nitroisoquinoline/8-bromo-5-nitroisoquinoline: >97%/<1%/<1%/<1 %.

References:

1. Gordon M. and Pearson D. E., *J. Org. Chem.*, 29 (1964) 329.

2. Butler J. L., Bayer F. L. and Gordon M., *Trans K Y. Acad. Sci.*, 38 (1977) 15.

3. Mathison I. W. and Morgan P. H., *J. Org. Chem.*, 39 (1974) 3210.
4. Rey M., Vergnani T. and Dreiding A. S., *Helv. Chim. Acta.*, 68 (1985) 1828.
5. Glyde E. and Talor R., *J Chem. Soc. Perkin Trans II*, (1975) 1783.
6. Robinson R. A., *J. Am. Chem. Soc.*, 69 (1947) 1942.
7. De La Mare P. B. D. Kiamud-din M. and Ridd J. H., *J. Chem. Soc.*, (1960) 561.
8. De La Mare P. B. D. Kiamud-din M. and Ridd J. H., *Chem. Ind.* (London), (1958) 361.
9. Osburn A. R., Schofield K. and Short L. N., *J. Chem. Soc.*, (1956) 4191.
10. Gottardi W., *Monat. Chem.*, 99 (1968) 815–822.

What is claimed is:

1. A process for the preparation of 5-or 8-bromoisoquinoline, or a derivative thereof, comprising the steps of:
   (i) reacting isoquinoline, or a derivative thereof, with a brominating agent, Z—Br, wherein Z represents a nitrogen containing heterocyclic group attached to said Br at a ring nitrogen or a secondary amino group of the formula $R_2N$—, wherein R is selected from the group consisting of an alkyl group, aryl group, acyl group and a sulfonyl group, in the presence of an aqueous solvent and in the presence of $H^+$ or a Lewis acid as catalyst; and
   (ii) isolating the product.

2. The process according to claim 1, wherein the 5- or 8-bromoisoquinoline is subjected to a nitrating agent of the formula $MNO_3$, wherein M represents a metal or $H^+$, to obtain a 5-bromo-8-nitroisoquinoline or a 5-nitro-8-bromoisoquinoline.

3. The process according to claim 1 for the preparation of a 5- or 8-bromoisoquinoline derivative, comprising the steps of:
   (i) reacting isoquinoline with the brominating agent in the presence of a catalyst to obtain a 5- or 8-bromoisoquinoline;
   (ii) reacting the 5- or 8-bromoisoquinoline obtained according to step (i) with a nitrating agent of the formula $MNO_3$, wherein M represents a metal or $H^+$; and
   (iii) isolating the 5- or 8-bromoisoquinoline derivative.

4. The process according to claim 1, wherein the leaving group Z is N-bromosuccinimide (NBS), N,N'-dibromoisocyanuric acid (DBI), or N,N'-dibromohydantoin (DBH).

5. The process according to claim 1, wherein the Lewis acid is $BF_3$, $AlX_3$, $TiX_4$, $ZnX_2$, $MnX_2$, $FeX_3$, $FeX_2$, $SnX_2$, $PbX_2$, $SbX_3$, or $SbX_5$ wherein X represents halogen.

6. The process according to claim 1, which is carried out as a "one pot" process.

7. A process for the preparation of 5- or 8-bromoisoquinoline comprising the steps of:
   (i) reacting isoquinoline with a brominating agent, Z—Br, in the presence of $H^+$ or a Lewis acid as a catalyst, wherein Z represents a nitrogen containing heterocyclic group attached to said Br at a ring nitrogen or a secondary amino group of the formula $R_2N$—, wherein R is selected from the group consisting of an alkyl group, aryl group, acyl group and a sulfonyl group; and
   (ii) isolating product.

8. The process according to claim 7, wherein the brominating agent is N-bromosuccinimde, N,N'-dibromoisocyanuric acid or N,N'-dibromohydantoin.

9. A process for the preparation of 5-bromo-8-nitroisoquinoline or 8-bromo-5-nitroisoquinoline comprising the steps of:
   (i) reacting isoquinoline with a brominating agent, Z—Br, in the presence of a catalyst, wherein Z represents a nitrogen containing heterocyclic group attached to said Br at a ring nitrogen or a secondary amino group of the formula $R_2N$—, wherein R is selected from the group consisting of an alkyl group, aryl group, acyl group and a sulfonyl group to form 5- or 8-bromoisoquinoline;
   (ii) reacting the 5- or 8-bromoisoquinoline obtained in step (i) with a nitrating agent of the formula $MNO_3$, wherein M represents a metal or $H^+$; and
   (iii) isolating the product.

10. The process according to claim 9, wherein the brominating agent is N-bromosuccinimde, N,N'-dibromoisocyanuric acid or N,N'-dibromohydantoin.

11. The process for the preparation of 5- or 8-bromoisoquinoline according to claim 1, wherein the catalyst is an acid with or without water.

12. The process for the preparation of 5- or 8-bromoisoquinoline according to claim 11, wherein the catalyst is selected from the group consisting of $FSO_3H$, $ClSO_3H$, $CF_2SO_3H$, $H_2SO_4$, $CH_3SO_3H$, $H_3PO_4$, polyphosphoric acid, $H_3PO_3$, $HXO_3$, $HXO_2$, HXO, HX, $CF_3COOH$ and $CH_3COOH$, wherein X represents halogen.

13. The process for the preparation of 5- or 8-bromoisoquinoline according to claim 9, wherein the catalyst is a Lewis acid selected from the group consisting of $BF_3$, $AlX_3$, $TiX_4$, $ZnX_2$, $MnX_2$, $FeX_3$, $FeX_2$, $SnX_2$, $PbX_2$, $SbX_3$ and $SbX_5$, where X represents halogen.

14. The process for the preparation of 5- or 8-bromoisoquinoline according to claim 9, wherein the catalyst is $H^+$ or a Lewis acid.

15. The process for the preparation of 5- or 8-bromoisoquinoline according to claim 9, wherein the catalyst is an acid with or without water.

16. The process for the preparation of 5- or 8-bromoisoquinoline according to claim 9, wherein the catalyst is selected from the group consisting of $FSO_3H$, $ClSO_3H$, $CF_2SO_3H$, $H_2SO_4$, $CH_3SO_3H$, $H_3PO_4$, polyphosphoric acid, $H_3PO_3$, $HXO_3$, $HXO_2$, HXO, HX, $CF_3COOH$ and $CH_3COOH$, wherein X represents halogen.

17. The process for the,preparation of 5- or 8-bromoisoquinoline according to claim 14, wherein the catalyst is a Lewis acid selected from the group consisting of $BF_3$, $Alx_3$, $TiX_4$, $ZnX_2$, $MnX_2$, $FeX_3$, $FeX_3$, $SnX_2$, $PbX_2$, $SbX_3$ and $SbX_5$, where X represents halogen.

18. The process for preparation of 5- or 8-bromoisoquinoline according to claim 9, wherein the process is a "one pot" process.

* * * * *